United States Patent [19]

Murayama et al.

[11] Patent Number: 5,633,070
[45] Date of Patent: May 27, 1997

[54] ADHESIVE FILM FOR ADHESIVE BANDAGE AND ADHESIVE BANDAGE USING SAID ADHESIVE FILM

[75] Inventors: Etsuo Murayama, Kohriyama; Toshikazu Saito, Sukagawa, both of Japan

[73] Assignee: Johnson & Johnson Consumer Products, Inc., Skillman, N.J.

[21] Appl. No.: 403,618

[22] Filed: Mar. 14, 1995

[30] Foreign Application Priority Data

Mar. 14, 1994 [JP] Japan ................................. 6-068209

[51] Int. Cl.⁶ ................................. B32B 23/02
[52] U.S. Cl. ................................. 428/194; 428/40.1; 428/516; 602/54; 602/55; 602/58; 602/59; 602/77; 442/329; 442/394; 442/398
[58] Field of Search ................................. 428/194, 40, 290, 428/343, 354, 230, 231, 245, 246, 265, 272, 516, 40.1; 602/54, 55, 58, 59, 77

[56] References Cited

U.S. PATENT DOCUMENTS

| | | | |
|---|---|---|---|
| Re. 31,886 | 5/1985 | Hodgson | 428/40.1 |
| 4,632,860 | 12/1986 | D'Antonio | 428/290 |
| 5,061,258 | 10/1991 | Martz | 604/307 |
| 5,431,991 | 7/1995 | Quantrille | 428/109 |

Primary Examiner—Nasser Ahmad

[57] ABSTRACT

An adhesive film for adhesive bandage in which an adhesive is coated on one surface of a nonwoven fabric, characterized in that a film having water vapor permeability and water proofing property is laminated on the opposite surface of the nonwoven fabric. A backing sheet is formed in such a structure that an elastic nonwoven fabric is laminated with a film having water vapor permeability and water proofing property, whereby sufficient flexibility and excellent water vapor permeability are provided and help to keep skin respiration and not only to prevent skin irritation caused by stickiness with perspiration or the like but also to completely prevent permeation of water, a detergent aqueous solution or the like into a pad portion or an affected part and further to prevent infection of a wound with bacteria. The preventions can be more completed by sealing the edge portion of the adhesive bandage via heat-sealing or the like. Further, the use of the laminating film can realize improvement in break strengths and abrasion resistance of the adhesive bandage, and improve handling characteristics in adhering the adhesive bandage to the affected part.

11 Claims, No Drawings

ADHESIVE FILM FOR ADHESIVE BANDAGE AND ADHESIVE BANDAGE USING SAID ADHESIVE FILM

DETAILED DESCRIPTION OF THE INVENTION

This invention relates to an adhesive film for adhesive bandage and an adhesive bandage using the adhesive film for adhesive bandage. More specifically, this invention relates to an adhesive film for adhesive bandage having water vapor permeability and water proofing property, wherein a nonwoven fabric having air permeability is used as a backing sheet of an adhesive bandage and a film having water vapor permeability and water proofing property is laminated on the nonwoven fabric, and to an adhesive bandage using said adhesive film.

Prior Art and Problems the Invention Seeks to Solve

Films of polyvinyl chloride, polyethylene, polypropylene and the like have been used in many cases as a backing sheet of an adhesive film for adhesive bandage. However, these films of polyvinyl chloride, polyethylene, polypropylene and the like are inferior in air permeability and water vapor permeability. Accordingly, when said films are used in an adhesive bandage, they hinder skin respiration in adhering to a skin, making the skin damp with perspiration. As a result, skin irritation is liable to occur. In order to prevent it and impart sufficient water vapor permeability, it is necessary to use a sufficiently thin film. On the other hand, when the film is made thin, stiffness is decreased owing to its softness and this makes it difficult to adhere the adhesive bandage to an affected part, thus causing a trouble; consequently, it tends to spoil a practical use. When using a thin film in consideration of such defects, there has been carried out a method in which a support formed of the other film is employed for ease of adhering. However, this method is undesirable because a procedure of adhering to the affected part is intricate. When these films are used as the backing sheet, there has been generally taken, for example, a measure of providing air holes. In this measure as well, skin respiration is locally hindered in other portions than the air holes. Besides, the air holes cause water to permeate into a pad portion. Thus, water proofing property has not been enough.

In this connection, proposals have lately been made in which air permeability and water vapor permeability are improved by using backing sheets which are formed of nonwoven fabrics composed of materials such as polystyrene, polyurethane, rayon and the like. These proposals can eliminate the aforesaid drawback of hindering skin respiration from qualities of these nonwoven fabrics, but involve a problem that water is permeated into the pad portion. Further, when waterproofing treatment is carried out with a silicone resin, a fluorine containing resin or the like, permeation of water can be prevented to some extent, but it is hard to completely prevent permeation of a solution of a surface active agent having low surface tension, such as a detergent or the like. Besides, to form adhesive films for adhesive bandage using said backing sheets, properties such as strength, chemical resistance, etc. are further required. This invention aims to provide an adhesive film for adhesive bandage having water proofing property while sufficiently securing water vapor permeability, which film has been so far unexpected.

Means for Solving the Problems

This invention aims to solve the above problems by laminating a film having water vapor permeability and water proofing property on a nonwoven fabric and coating an adhesive having water vapor permeability and/or coating the adhesive in pattern state on the nonwoven fabric. That is, this invention relates to an adhesive film for adhesive bandage in which an adhesive having water vapor permeability is coated on one surface of a nonwoven fabric or an adhesive is coated thereon such that water vapor permeability is provided, characterized in that a film having water vapor permeability and water proofing property is laminated on the surface of the nonwoven fabric. More specifically, this invention relates to an adhesive film for adhesive bandage, in which an adhesive having water vapor permeability, preferably a porous adhesive is coated or pattern-coated or a adhesive is pattern-coated on the surface of a backing sheet obtained by laminating a film having water vapor permeability and water proofing property, such as a polyurethane film, a polyolefin film or the like on an elastic nonwoven fabric of a polystyrene-type polymer, a polyurethane, a polyester or the like.

The nonwoven fabric used in this invention can be any nonwoven fabric if having air permeability and elasticity. Especially preferable are known nonwoven fabrics which are formed from elastomer filaments made of polystyrene elastomers such as a styrene-isoprene-styrene block copolymer, a hydrogenated styrene-isoprene-styrene block copolymer, etc., polyurethanes, polyesters and mixtures thereof. They are, however, not critical. It is advisable that the nonwoven fabric has percent expansion of 100% or more, a recovery rate in 50% expansion of 70% or more and a weight of 20 to 200 g/m$^2$.

The weight of the nonwoven fabric used in this invention has to be properly selected depending on properties of the nonwoven fabric itself and properties of the adhesive, and cannot particularly be limited. However, it is preferably 20 to 200 g/m$^2$, more preferably 30 to 100 g/m$^2$. A thickness of the nonwoven fabric may be such a thickness that a sufficient stiffness is imparted to the adhesive film for adhesive bandage when laminating the laminating film on the nonwoven fabric. The nonwoven fabric can be thinner than a nonwoven fabric used in an ordinary adhesive bandage. The thickness of the nonwoven fabric is about 20 to 1,000 μm, preferably 50 to 500 μm.

The film as a laminating film of the nonwoven fabric in this invention is used to impart water proofing property to the adhesive bandage without much impairing air permeability and water vapor permeability of the nonwoven fabric and to give a suitable balance of properties when forming it into the adhesive bandage. The material of the film is required to have water proofing property and to still keep water vapor permeability when laminated on the nonwoven fabric. For providing such properties, the film has to be one which can permeate water vapor but prevent permeation of water. As this film, known films formed of polyurethanes, polyolefins, polyvinyl chloride, and so forth can be used. Of these, polyurethane films and polyolefin films are preferred because of their high water proofing property, high water vapor permeability and suitable elasticity. Since the laminating film is required to have sufficient water proofing property, a film obtained by extrusion molding, blow-molding or the like is desirous. A stretched film is also available. Said laminating film can be also a multilayered film formed by laminating films made of different materials.

If the material of the film used as the laminating film has low water vapor permeability, it has to be rendered thinner for securing water vapor permeability. If the material of the laminating film has high water vapor permeability, it can be rendered thicker, but has to have suitable stiffness when laminated on the nonwoven fabric. From this standpoint, the thickness of said film is preferably 50 μm or less, especially preferably 2 to 30 μm, more preferably 5 to 15 μm. Since properties can easily be balanced by laminating the film on the nonwoven fabric, it is possible to use a wide-ranging nonwoven fabric, especially, a so-called less stiff, thin nonwoven fabric and to readily improve strength and chemical resistance. A method for laminating the film on the nonwoven fabric is not particularly limited, but the laminating can be carried out by bonding with a bonding agent, heat-fusion or the like. The laminating may be conducted on the nonwoven fabric either before or after coating the adhesive thereon.

The adhesive used in the adhesive film for adhesive bandage of this invention is not particularly limited if a skin is little irritated and pressure-sensitive adhesion to the skin is provided. Examples of the adhesive include a rubbery adhesive, an acrylic adhesive, a polyurethane adhesive, a silicone adhesive and a styrene-isoprene-styrene block copolymer adhesive.

Such adhesive can be coated on the whole adhesive surface of the nonwoven fabric. However, to prevent decrease in water vapor permeability, it is preferred to coat a porous adhesive or pattern-coat the adhesive without coating it on the whole surface.

As a method for making the adhesive porous, there is, for example, a method in which a highly water-absorbable polymer is used as a blowing agent, water is fully absorbed therein, the resulting polymer is dispersed into an adhesive solution, the dispersion is coated, and a moisture is then evaporated to make the adhesive porous. This method is, however, not critical.

Regarding the pattern coating, the adhesive can be coated on the backing sheet by, for example, screen coating or gravure coating. However, these coatings are not critical.

As a method for coating the adhesive on the backing sheet, there can be taken various known methods such as a method in which the adhesive is directly coated on the nonwoven fabric, a method in which the adhesive is coated on a release paper and then transferred onto the nonwoven fabric, and the like.

In the adhesive bandage using the adhesive film for adhesive bandage in this invention, when the adhesive bandage is cut, an exposed portion of the nonwoven fabric appears in a cut edge portion. When water or a surface active agent solution is permeated from said edge portion, the edge portion can be sealed by heat sealing, pressure-bonding or the like to improve water proofing property.

The adhesive film for adhesive bandage in this invention can almost completely prevent permeation of a liquid such as water, the surface active agent solution or the like from the film surface.

The adhesive film for adhesive bandage in this invention may be formed into an adhesive bandage by any method. Examples of the method include a method in which a long film having a suitable width is wound up to form an adhesive bandage, a method in which a film sheet of suitable size is provided, a water-absorbable pad is held on the central portion of the sheet, and an adhesive surface is further covered with a release paper to form an individual pack of an adhesive bandage, a method in which a sheet of suitable size is provided, and an adhesive surface is covered with a release paper without placing a pad to form an individual pack of an adhesive bandage, and so forth.

This invention will be explained more specifically by referring to the following Examples.

EXAMPLES

In Examples, properties were evaluated according to the following methods.

(1) Modulus:

A sample was cut into ribbons having a width of 25.4mm (1 inch), and the ribbons were mounted on a tensile tester at intervals of 50mm. A weight load was measured when the test pieces were drawn 5%, 10% and 100% at a pulling rate of 100mm/min., and stress per 1 cm width of the test piece was measured.

(2) Tensile strength at break and tensile elongation at break:

A sample was cut to a width of 25.4mm (1 inch), and the cut pieces were mounted on a tensile tester at intervals of 50mm. A pulling rate was set at 100mm/min., and a weight load and elongation were measured when the test pieces were broken.

(3) Adhesion to glass:

A sample was cut to a width of 25.4mm (1 inch) and bonded to a glass well washed with acetone. A weight load was exerted on the resulting glass by one reciprocation with a roller in which a rubber was wound on an iron core having a weight of 4.5 kg. A pulling rate was set at 300mm/min., and a load weight was measured when the test pieces were peeled off from the glass surface.

(4) Water vapor permeability:

A sample film was bonded to a ring of a water vapor permeation cup according to JIS Z 0208, and surely mounted on a guide provided therein with a laboratory dish filled with water. The sample placed on the guide was put in a constant-temperature (32° C.)/constant-humidity (30 RH %) chamber. A weight was measured hourly, and the measurement was repeated until a weight difference per hour became stable. Water vapor permeability (g/m$^2$·24 hrs.) was calculated from a value of change in weight per hour. Water vapor permeability of a human skin is considered about 1,000 g/m$^2$·24 hrs. Then, water vapor permeability was evaluated according to the following rates.

| more than 1,500 (g/m$^2$ · 24 hrs.) | ⊙ |
| 1,500–800 (g/m$^2$ · 24 hrs.) | ○ |
| 800–300 (g/m$^2$ · 24 hrs.) | △ |
| less than 300 (g/m$^2$ · 24 hrs.) | × |

(5) Water proofing property:

0.1 Milliliter of water or a 0.75% detergent aqueous solution was dropped on a surface of a sample under indoor atmosphere from a height of 2 cm. There was measured a time that lapsed from the time when the liquid was dropped to the time when the liquid was completely permeated into the sample. Upon comparing the results obtained by this method with a state when the sample was actually adhered to a skin, the results are as follows. When the liquid was permeated into the sample within 1 hour by this method, said liquid was readily permeated into the adhesive bandage in actual use by expansion of the film, rubbing with the skin, and so forth, and water proofing property was not observed. On the other hand, when the liquid was not permeated for more than 3 hours, permeation was substantially not observed in actual use. Water proofing property was therefore evaluated according to the following rates.

| Water proofing property | |
| --- | --- |
| more than 3 hours | ◉ |
| 1–3 hours | Δ |
| less than 1 hour | × |

Example 1

A styrene-isoprene-styrene block copolymer containing 27% by weight of polystyrene and polypropylene were mixed in pellet state such that the content of polypropylene became 30% by weight. After they were melt-mixed by an extruder, the mixture was injected through a melt-blow spinning apparatus to form fibers. The fibers were collected, and pressure-bonded under heat to form a nonwoven fabric (trade name: Septon, made by Kuraray Co., Ltd.). A weight of the nonwoven fabric was 70 g/m². A 10 μm-thick polyurethane film (made by Tokunaga Boeki K.K.) was laminated on one surface of the nonwoven fabric by heat fusion. Subsequently, an acrylic adhesive having dispersed therein a highly water-absorbable polymer (trade name: Sun Wet, made by Sanyo Kasei K.K.) was coated on the opposite surface of the nonwoven fabric such that the thickness became 50 μm, and the coated film was dried to obtain an adhesive film for adhesive bandage wherein the acrylic adhesive was rendered porous. This adhesive film was used as a sample and measured for (1) modulus, (2) tensile strength at break and tensile elongation at break, (3) adhesion to glass, (4) water vapor permeability and (5) water proofing property. The results of these evaluations are shown in Table 1.

elastomer filaments and heat-fusing them. An acrylic adhesive having dispersed therein a highly water-absorbable polymer as a blowing agent was coated on the opposite surface of the nonwoven fabric, and dried to make the acrylic adhesive porous. There was thus obtained an adhesive film for adhesive bandage. Said adhesive film was evaluated in the same manner as in Example 1. The results of the evaluations are shown in Table 1.

Example 4

The same 10 μm-thick polyurethane film as used in Example 1 was laminated on one surface of a nonwoven fabric (made by Kuraray Co., Ltd.) having a weight of 50 g/m², which was obtained by accumulating polyester elastomer filaments. An acrylic adhesive having dispersed therein a highly water-absorbable polymer as a blowing agent was coated on the opposite surface of the nonwoven fabric, and dried to make the acrylic adhesive porous. There was thus obtained an adhesive film for adhesive bandage. Said adhesive film was evaluated in the same manner as in Example 1. The results of the evaluations are shown in Table 1.

Comparative Example 1

A 75 μm-thick vinyl chloride film (made by Johnson & Johnson K.K.) was used as a backing sheet. A raw rubber-type adhesive was coated on one surface of said film to a thickness of 50 μm. There was thus obtained an adhesive film similar to an adhesive film used in a commercial adhesive bandage. The results of the evaluations are shown in Table 1. Since the sample in Comparative Example 1 is low in water vapor permeability, it seems likely to hinder

TABLE 1

| Test item | (unit) | Example No. 1 | 2 | 3 | 4 | Comparative Example No. 1 | 2 |
| --- | --- | --- | --- | --- | --- | --- | --- |
| Modulus 5% | (g/cm) | 95 | 98 | 75 | 71 | 59 | 94 |
| Modulus 10% | (g/cm) | 142 | 154 | 102 | 106 | 102 | 157 |
| Modulus 100% | (g/cm) | 291 | 299 | 240 | 173 | 717 | 374 |
| Tensile strength at break | (g/cm) | 728 | 677 | 713 | 665 | 1500 | 524 |
| Tensile elongation at break | (%) | 583 | 567 | 609 | 603 | 340 | 391 |
| Adhesion to glass | (g/cm) | 260 | 244 | 240 | 220 | 146 | 165 |
| Water vapor permeability | (g/m² · 24 hrs) | 1730 | 1720 | 1670 | 1770 | 35 | 910 |
| <Evaluation of water vapor permeability> | | ◉ | ◉ | ◉ | ◉ | × | ◉ |
| Water proofing property | (hrs) | >3 | >3 | >3 | >3 | >3 | >3 |
| Water proofing to a detergent aqueous solution | (hrs) | >3 | >3 | >3 | >3 | >3 | <1 |
| <Evaluation of water proofing property> | | ◉ | ◉ | ◉ | ◉ | ◉ | × |
| General evaluation | | ◉ | ◉ | ◉ | ◉ | × | × |

Example 2

An adhesive film for adhesive bandage was obtained in the same manner as in Example 1 except that the weight of the nonwoven fabric was 50 g/m². Said adhesive film was evaluated in the same manner as in Example 1. The results are shown in Table 1.

Example 3

The same 10 μm-thick polyurethane film as used in Example 1 was laminated on one surface of a nonwoven fabric (made by Kuraray Co., Ltd.) having a weight of 50 g/m², which was obtained by accumulating polyurethane skin respiration and cause occurrence of skin irritation due to stickiness with perspiration. This result shows that when the polyvinyl chloride film is used, it is necessary to secure water vapor permeability, and some measure has to be taken, such as formation of holes in the film or the like.

Comparative Example 2

The same nonwoven fabric as used in Example 1 was subjected to waterproofing treatment with a fluorine-containing resin. In the same manner as in Example 1, an acrylic adhesive having dispersed therein a highly water-absorbable polymer as a blowing agent was coated on one surface of the nonwoven fabric such that the thickness becomes 50 μm, and dried to obtain an adhesive film for adhesive bandage wherein the acrylic adhesive was rendered porous. The results of the evaluations are shown in Table 1. Table 1 reveals that in case of the nonwoven fabric having no laminating film, water proofing property to the detergent aqueous solution is inferior even if the waterproofing treatment is conducted, and it is thus undesirable.

From all the results in Table 1, it becomes apparent that since the adhesive film for adhesive bandage in this invention is rich in flexibility and excellent in fitness to a skin and also in water vapor permeability, skin respiration can be kept and the trouble caused by stickiness with perspiration can be prevented. Further, the water vapor-permeable film is laminated on the nonwoven fabric, making it possible to prevent permeation of the liquid such as water, etc. into the absorption pad and the affected part, enhance break strengths and prevent fluffing and contamination that occur by rubbing the nonwoven fabric.

Effects of the Invention

In the adhesive bandage using the adhesive film for adhesive bandage in this invention, a backing sheet is formed in such a structure that an elastic nonwoven fabric is laminated with a film having water vapor permeability and water proofing property, whereby sufficient flexibility and excellent water vapor permeability are provided and help to keep skin respiration and not only to prevent skin irritation caused by stickiness with perspiration or the like but also to completely prevent permeation of water, a detergent aqueous solution or the like into a pad portion or an affected part and further to prevent infection of a wound with bacteria. The preventions can be more completed by sealing the edge portion of the adhesive bandage via heat-sealing or the like. Further, the use of the laminating film can realize improvement in break strengths and abrasion resistance of the adhesive bandage, and improve handling characteristics in adhering the adhesive bandage to the affected part.

We claim:

1. An adhesive film for an adhesive bandage, said adhesive film comprising an elastic, air permeable nonwoven fabric, one surface of said nonwoven fabric being coated with a water vapor permeable adhesive, the other surface of said nonwoven fabric having laminated thereto a water impermeable, water vapor permeable film, said nonwoven fabric comprising elastomeric filaments comprising a styrene-isoprene-styrene block copolymer.

2. An adhesive film for an adhesive bandage, said adhesive film comprising an elastic, air permeable nonwoven fabric, one surface of said nonwoven fabric being coated with a water vapor permeable adhesive, the other surface of said nonwoven fabric having laminated thereto a water impermeable, water vapor permeable film, said nonwoven fabric comprising elastomeric filaments formed from a mixture of polypropylene and a styrene-isoprene-styrene block copolymer.

3. The adhesive film of claim 2 wherein said mixture comprises 70% by weight of said styrene-isoprene-styrene block copolymer and 30% by weight of polypropylene.

4. The adhesive film of claim 3 wherein said styrene-isoprene-styrene block copolymer contains 27% by weight polystyrene.

5. The adhesive film of claim 1 wherein said adhesive is porous.

6. The adhesive film of claim 1 wherein said adhesive is pattern-coated.

7. The adhesive film of claim 1 wherein an edge portion has been subjected to a sealing treatment.

8. The adhesive of claim 1 wherein said laminated film is selected from the group consisting of polyurethane film and polyolefin film.

9. The adhesive film of claim 1 wherein said laminated film is a polyurethane film.

10. An adhesive bandage comprising the adhesive film of claim 1.

11. An adhesive bandage comprising the adhesive film of claim 2.

* * * * *